(12) United States Patent
Purdum

(10) Patent No.: US 6,196,965 B1
(45) Date of Patent: Mar. 6, 2001

(54) COMPOSITIONS METHODS AND DEVICES FOR EMBRYO IMPLANTATION FOR IN VITRO FERTILIZATION

(75) Inventor: Howard E. Purdum, Alpharetta, GA (US)

(73) Assignee: Cryofacets, Inc., Alpharetta, GA (US)

( * ) Notice: Subject to any disclaimer, the term of this patent is extended or adjusted under 35 U.S.C. 154(b) by 0 days.

(21) Appl. No.: 09/316,799

(22) Filed: May 21, 1999

Related U.S. Application Data

(60) Provisional application No. 60/086,316, filed on May 21, 1998.

(51) Int. Cl.[7] .................................................. A61B 17/43
(52) U.S. Cl. ................................................................ 600/34
(58) Field of Search ........................ 600/33–35; 604/514, 604/515

(56) References Cited

U.S. PATENT DOCUMENTS

| | | | | |
|---|---|---|---|---|
| 4,701,161 | * | 10/1987 | Lenck | 604/55 |
| 5,360,389 | * | 11/1994 | Chenette | 600/34 |
| 5,747,659 | | 5/1998 | Fioretti et al. | 536/23.4 |
| 5,820,613 | * | 10/1998 | Van Werven-Franssen | 604/282 |
| 5,938,582 | * | 8/1999 | Ciamacco, Jr. et al. | 600/3 |
| 5,961,444 | * | 10/1999 | Thompson | 600/33 |
| 6,010,448 | * | 1/2000 | Thompson | 600/34 |

OTHER PUBLICATIONS

The Use of Fibrin Sealant in In Vitro Fertlization and Embryo Transfer, Zion Ben–Rafael, M.D., et al., 1995, International J. Fertil., vol. 40, No. 6, pp. 303–306.

The Use of Fibrin Sealant For Embryo Transfer: Development and Clinical Studies, Wilfried Feichtinger, et al., Human Reproduction, vol. 7, No. 6, pp. 890–893, 1992.

The Effect of Fibrin Sealant on Mouse Embryos, F.A. Rodrigues, et al., 1988, Journal of In Vitro Fertilization and Embryo Transfer, vol. 5, No. 3, pp. 158–160.

The use of two–component fibrin sealant for embryo transfer, Wilfried Feichtinger, M.D., et al., Fertility and Sterility, vol. 54, No. 4, Oct. 1990, pp. 733–734.

Transfusion Medicine, Jeffrey McCullough, M.D., University of Minnesota, Department of Laboratory Medicine, Minneapolis, Minnesota, pp. 79–81.

Platelet Gel: An Autologous Alternative to Fibrin Glue With Applications in Oral and Maxillofacial Surgery, Dean H. Whitman, DDS, et al., J. Oral Maxillofac Surg. 55: pp. 1294–1299, 1997.

Patterns of expression of integrin molecules in human endometrium throughout the menstrual cycle, S. Tabibzadeh, Human Reproduction, vol. 7, No. 6, pp. 876–882, 1992.

* cited by examiner

*Primary Examiner*—John P. Lacyk
(74) *Attorney, Agent, or Firm*—Kilpatrick Stockton, LLP

(57) ABSTRACT

The present invention is directed to compositions and apparatus to be used in methods of implantation of embryos for in vitro fertilization. The methods include insertion of embryos that have attached adhesives. Such methods, compositions and apparatus can be used with any mammals, including humans, farm animals and exotic or endangered animals.

27 Claims, 3 Drawing Sheets

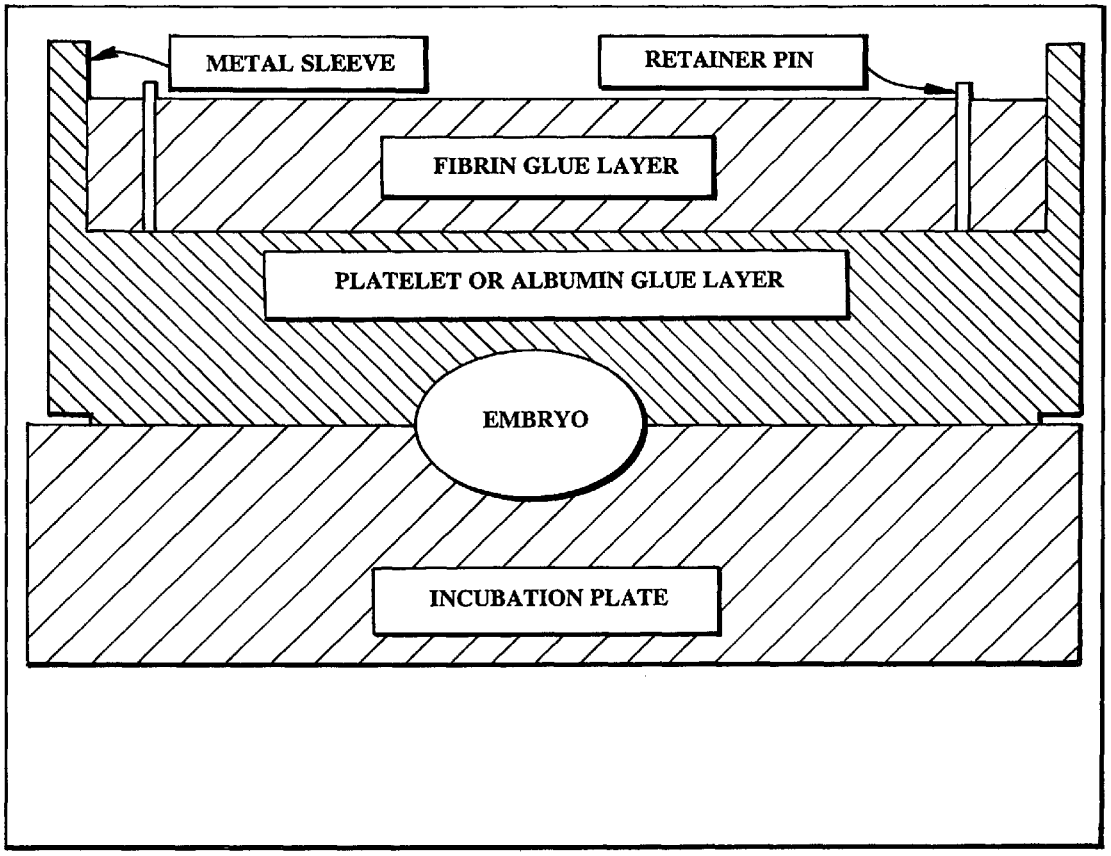
Fig_1
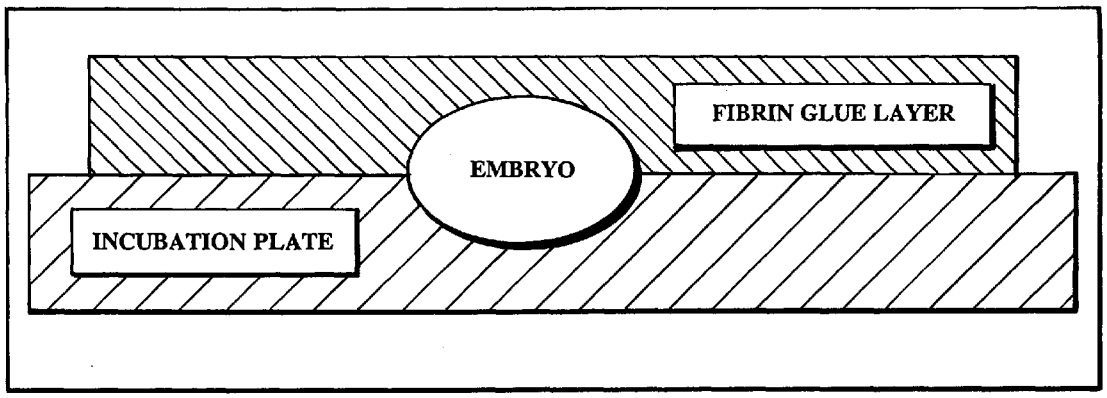
Fig_2

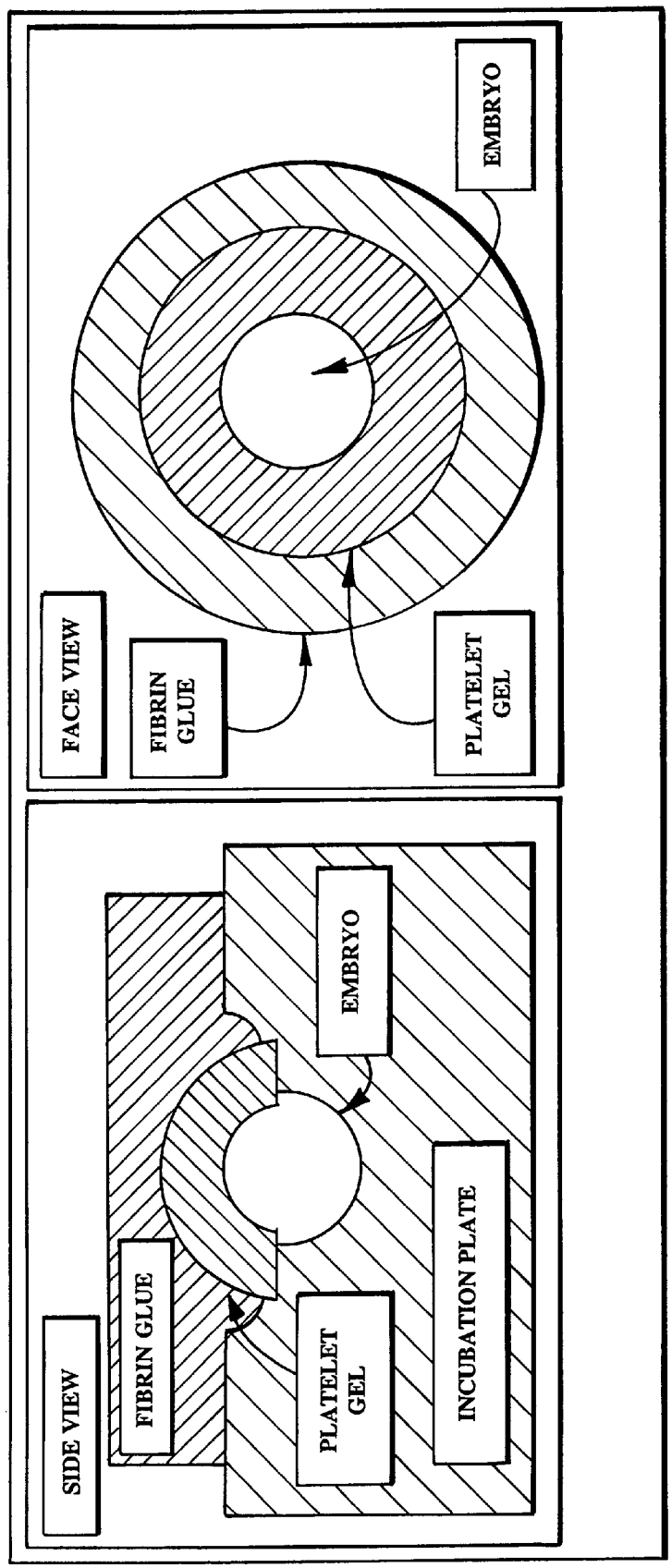

COMPOSITIONS METHODS AND DEVICES FOR EMBRYO IMPLANTATION FOR IN VITRO FERTILIZATION

RELATED APPLICATION

This application claims priority to a provisional application, U.S. Ser. No. 60/086,316, filed May 21, 1998, which is herein incorporated in its entirety.

TECHNICAL FIELD

The present invention relates to compositions, methods and devices for in vitro fertilization. More particularly, the present invention relates to compositions, methods and devices to aid in implantation of embryos.

BACKGROUND OF THE INVENTION

Treatment of infertility problems is a growing area of health care. Approximately 50,000 human in vitro fertilization (IVF) procedures are performed in the US annually. Although costs vary widely depending on drugs, testing and other laboratory fees, typical IVF charges are on the order of $10,000 per procedure, not counting travel, lost work time, and emotional costs for the patients. Additionally, in treatment of animals, the ability to control the birth of offspring is important for agricultural concerns and for preservation of endangered species.

Many approaches are being developed to resolve problems with infertility. Infertility is understood to be the inability to conceive after six to twelve months of sexual activity without the use of contraceptives, depending on the age of the persons involved. Because infertility exerts extreme physical, emotional and financial stresses on those who are unable to conceive, there is a great need for improved aids for reproduction. These aids are typically referred to as Assisted Reproductive Technologies (ART). By far the most common ART component is IVF, which has grown explosively in the two decades since it was developed. In its simplest form, IVF consists of pharmaceutical stimulation of the female's ovaries to produce a large number of follicles. Eggs surgically harvested from these follicles are then mixed in the laboratory with the male's sperm. If fertilization is successful, the embryos are incubated for a short time and then transferred back to the female. If one of these embryos implants in the uterine wall, a successful pregnancy may follow.

There are several modifications of this basic technique. For example, intracytoplasmic sperm injection (ICSI) can be used for cases of low sperm count or cases where the sperm has difficulty fertilizing the egg. Another IVF modification is Assisted Hatching (AH), a procedure in which the zona pellucida (the outer wall of the embryo) is mechanically cut or chemically etched, thereby partially exposing the embryo. In some laboratories, this procedure significantly improves implantation rates, particularly for older patients. Finally, IVF procedures can also incorporate donor tissues, including sperm, ova and embryos, for those individuals who cannot produce their own.

Despite its great successes, IVF has several significant problems. First and foremost, the procedure is unpredictable. Although the ideal result of any IVF procedure is a single, live birth, a viable pregnancy occurs in only about 30% of all procedures. Conversely, IVF may result in a pregnancy with multiple embryos. In this regard, twins and triplets pose relatively few risks beyond a single embryo pregnancy. The potential for problems, however, increases for higher order births. Selective embryo reduction is therefore often recommended for these cases which increases the psychological trauma for the parents.

Like unassisted reproduction, IVF begins with a source of sperm and ova. There is a virtually 100% certainty of obtaining these materials, using donor tissues if necessary. Next, fertilization occurs, and good IVF laboratories typically have a fertilization success rate of about 75%, using ICSI if appropriate. After a short incubation period, the resulting embryo is then introduced into the uterus, where implantation occurs. Implantation is generally the limiting factor in overall IVF success.

Implantation itself, however, consists of several steps. First, the embryo must enter the uterine cavity. In normal reproduction, without ART, the embryo descends through the fallopian tubes. The embryo then comes into contact with some point on the uterine wall. Next, the embryo and wall surfaces fuse at the contact point. The uterine wall properties then change dramatically at the implantation site, thus allowing the embryo to become fully implanted. For IVF, the embryo is carried into the uterine cavity in a solution injected from a syringe inserted through the cervical canal.

Although the implantation process appears to be simple enough, it is actually quite complicated and requires the coordination of many factors, some of which are unknown. A failure of any one of these processes prevents implantation and thus pregnancy. Furthermore, it is believed that implantation failures may indeed be the reason that only about 20% of even the most fertile couples conceive in a given month of attempting pregnancy.

Improving the implantation rate would make the IVF process more reliable, more effective and yield many benefits. Improving the effectiveness of the IVF process above its current 30% would reduce the need for repeat procedures, a critical factor considering the costs and stresses involved for the patients. Another benefit is that an improved success rate would make better use of the quite limited supply of donor ova and embryos. Improving the success rate would also further extend the supply of donor tissues by enabling some patients, particularly those who are older but otherwise healthy, to use their own tissues. Such patients would be more than willing to leave the donor program given the opportunity to have children of their own genetic basis. Yet another benefit is that by reducing the number of embryos required for a successful procedure, the incentive to overstimulate the ovaries is reduced, thereby reducing possible harmful side effects to the patient. Finally, improved implantation rates would eliminate the incentive to transfer large numbers of embryos back to the uterus, thereby preventing multiple births.

These advantages have been noted before, resulting in a variety of efforts to improve the implantation process, including both chemical and mechanical methods. The chemical techniques employ both natural and artificial compounds to improve the conditions of the embryo, the uterus, or both.

Many of these chemical efforts employ pharmaceutical modification of the uterine surface to make it more receptive to the embryo. Although these efforts are promising, there is concern that any agent strong enough to alter the properties of the uterus may also harm the embryo, thereby leading to birth defects. Another approach to improve implantation involves incubating the embryos to the blastocyst or later stages before transfer. Although this approach is promising, one European group has recently established an Internet registry to track the possibility of related birth defects. At the present time, none of these methods are effective in increasing the success at a viable pregnancy.

Mechanical means have focused on assisted hatching (AH) and tissue cultures. AH involves eroding the wall of the embryo by chemical and/or physical attack so that the embryo can expand and attach more readily, a technique particularly useful for patients over 38 years of age. Tissue cultures of uterine wall cells promise a more hospitable environment while still in vitro, with the hope that these conditions will prevail after transfer.

None of these techniques has produced much success. Thus, what is needed are compositions, methods and devices to aid in embryo transfer and implantation for in vitro fertilization.

SUMMARY OF THE INVENTION

The present invention relates to compositions, methods and devices for increasing the success of implantation of an embryo for in vitro fertilization. More particularly, the present invention relates to compositions, methods and devices for attaching an embryo to a surface that is then placed within the uterine cavity. Such compositions, methods and devices are contemplated for use in any animal system, including humans, and animal husbandry, such as cattle, sheep and swine, and for exotic animals. The following compositions and methods are intended as means to enhance the implantation rates now observed.

IVF is a complicated, sophisticated process. The present invention is directed to improving implantation rates by providing compositions and devices in methods for implantation. One immediate result of improved implantation rates is fewer total IVF procedures, with psychological, physical, and financial savings to the patient. Another immediate result is fewer embryos transferred at any given time, leaving more embryos for later transfer without requiring further retrieval. The present invention thus also reduces that likelihood of multiple births.

A preferred embodiment of the present invention is a combination of mechanical manipulation of the embryo with compositions capable of supporting and containing the embryo, or compositions and mechanical manipulations capable of enhancing the implantation of the embryo. The devices of the present invention can be used with any such advances to achieve ideal IVF success.

Accordingly, it is an object of the present invention to provide methods to aid in implantation for in vitro fertilization.

Another object of the present invention to provide compositions to aid in implantation for in vitro fertilization.

It is yet another object of the present invention to provide devices for aids in implantation for in vitro fertilization.

It is another object of the present invention to provide compositions, methods and devices that allow for the formation of a structure that holds one or more embryos in a stable form that is placed within the body to aid in implantation.

It is a further object of the present invention to increase the success rate of in vitro fertilization by aiding in the implantation of embryos.

BRIEF DESCRIPTION OF THE FIGURES

FIG. 1 shows a drawing of an embodiment of the present invention wherein two adhesives are used.

FIG. 2 shows a drawing of an embodiment of the adhesive/embryo structure wherein one adhesive is used.

FIG. 3 shows a side and face view of the embodiment of shown in FIG. 2.

DETAILED DESCRIPTION

Figure 4:
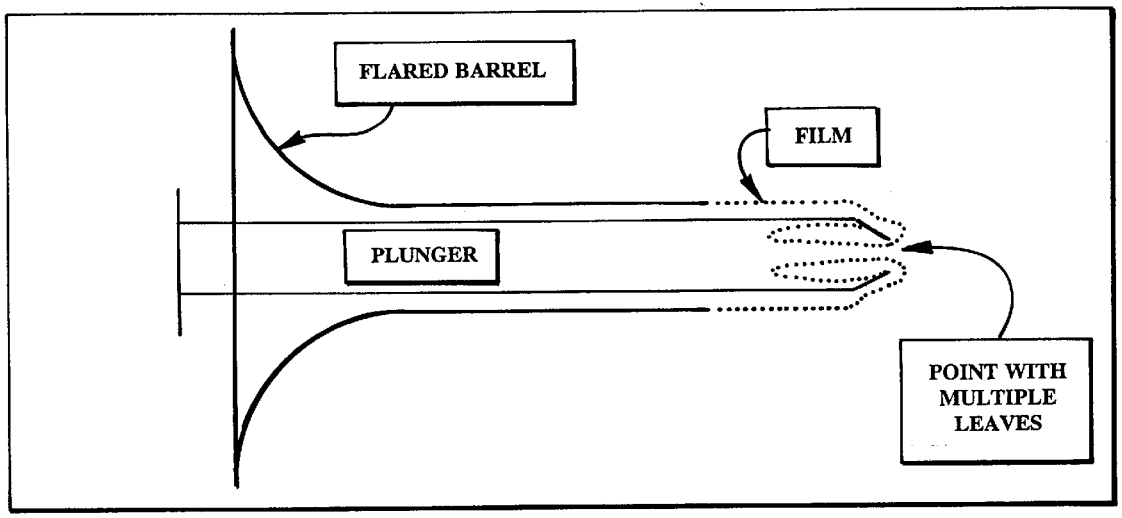
FIG. 4 shows an embodiment of an apparatus that can be used to insert an embryo.

The present invention comprises compositions, methods and devices to aid in implantation of embryos. These compositions, methods and devices are particularly advantageous for in vitro fertilization. Such methods and devices may be used for humans, but also may be used for animals or any other system where embryo implantation is used. As used herein, embryo includes a fertilized egg or other structure that is capable of developing into a new individual.

Most of the current IVF treatments are directed to changes in the uterine wall. For example, progesterone supplements are commonly prescribed to avoid the problems associated with luteal phase defects. Likewise, to improve the success rate of IVF procedures, biological markers in the uterine surface can be used passively for timing purposes, or the surface itself can be altered actively by pharmaceutical agents. Although these and similar approaches show significant promise, they nevertheless have the potential problem of inducing serious birth defects.

The work to date involving embryos has emphasized donor tissues, instead of pharmaceutical approaches. Specifically, it has been found that women in their later thirties and early forties using donor eggs have essentially the same fertility rate as the younger donors. A similar result holds for donor embryos, which is not surprising because sperm function changes relatively little over the normal paternal age range, leaving the effective age of the embryo to be that of the egg. With such advances in ART, even post-menopausal women can give birth, using appropriate hormone therapy. Preliminary work is currently under way at several IVF laboratories to remove most of the genetic material from the center of a donor egg and replace it with the older patient's material. The desired result is that the patient would have an egg of essentially her own genetic basis, while retaining the higher likelihood of pregnancy of the younger donor. Although no births have been reported to date, this technique does show significant promise.

Though not wishing to be bound by any particular theory, it is theorized that implantation depends on the uterine cavity being in contact with the embryo for a sufficient amount of time so that the necessary bonds can form. In particular, only one site of the uterine wall needs to be in contact with only one site of the embryo.

Of course, in nature this does not always happen. Instead, the embryo essentially bounces from site to site until a suitable site can be found. For in vitro processes, this situation is even worse, with the embryo floating in the suspension fluid before any attachment can be made. The time spent by the embryo by floating in the suspension fluid may account for some of the lower observed implantation rates for such processes.

Any preliminary attachment by the embryo is weak and extends only over a limited area, and bond rupture can occur readily, again leaving the embryo unattached. Such ruptures would be expected to be of particular concern for older patients because the tougher shell of the embryo would be less prone to form strong bonds quickly. Repeated ruptures thus eventually result in implantation failure, as often observed for older patients using their own eggs without AH.

Conversely, the use of AH or donor eggs leads to stronger bonds, in agreement with the enhanced implantation rates observed for these approaches.

This bonding requirement holds for all stages of embryo development prior to transfer, and the present invention can be used with blastocyst and all other alternative stage approaches. Likewise, the present invention can also be used with chemical treatments of the uterine wall or cavity that are known to those skilled in the art. Safe and effective pharmaceutical and/or advanced incubation processes can be used in a combination of these procedures with the present invention.

Though not wishing to be bound by any particular theory, the following theory of implantation is suggested. Mechanically, the limiting step in implantation is the first contact of the embryo with the uterine wall. At this juncture, the embryo has only a minimal contact area with the wall surface, compared to the much greater contact area that develops as the uterine wall eventually envelopes the embryo. Also at first contact, the bonds between the embryo and the wall are only just beginning to form, compared to the much stronger bonds that form as implantation proceeds. The net effect is that implantation begins with weak bonds joining only a small area of the embryo to the uterine wall, progressing to strong bonds over virtually the entire embryo surface.

As a direct clinical consequence of the progression of binding in implantation, IVF patients are advised to refrain from sexual intercourse, heavy lifting, or any other vigorous physical activity for at least two days after transfer. Such higher levels of activity can be safely tolerated later in the pregnancy after more secure attachment has been achieved by the embryo.

It is an object of the present invention to hold the embryo in continuous contact with a selected point of the uterus, and to enhance the bonding between the embryo and the uterine wall, thereby aiding the implantation of the embryo. Thus, the present invention includes, but is not limited to, embryo preparation plates, biological adhesives, and applicators.

An element of the present invention is a device for holding the embryo for further manipulations, the embryo preparation plate. The present invention contemplates a device that is capable of stabilizing the embryo so that the embryo can be manipulated in the manner of the methods of the present invention. No particular design is required by the present invention, and any device that holds the embryo without damage, and allows for the application of adhesives or other manipulations is contemplated by the present invention. A preferred device is a modification of a flat incubation plate so that the plate has hemispheric depressions the size of the embryo, including floatation space. Another embodiment is a flat plastic plate, containing a hemispherical depression with rounded edges. An inexpensive method for making such a plate comprises forcing a normal straight pin into the soft plastic of the plate, yielding a conical depression. An acid etch then removes the sharp edges to create the desired shape. For commercially produced devices, micromachining techniques are used to produce a high quality mold having the desired shape, which would then be used for mass production of plates with hemispheric depressions.

Other elements of the present invention include the compositions used with the embryo. For example, preferred compositions are adhesives, such as synthetic or biological adhesives. Biological adhesives have been used as hemostasis agents and for wound approximation. In surgical practice, biological adhesives are quite useful because they are easily prepared, they control bleeding quickly and effectively, they aid wound healing, and they leave little or no scarring. For these reasons, they have been used intensely in the past several years as replacements for sutures.

Biological adhesives are preferable because they promote healing, and because they are readily absorbed by the body after use. Although recent FDA rulings allow such agents to be obtained from homologous sources, autologous materials should obviously be used if at all possible for optimum tissue matching. Most preferably, the adhesives of the present invention are made from the patient's own tissues. Other types of adhesives that are known to those skilled in the art are also contemplated in the present invention.

One feature of the adhesives contemplated by the present invention is biocompatibility. The present invention contemplates both natural and synthetic adhesives that are biocompatible with either the embryo or the host, or both. Of the many such possible adhesives or glues that are contemplated by the present invention, the most preferred ones are based on collagen, albumin, platelets and fibrin. The platelet and albumin products have greater wound healing ability, but their bonds are inherently weaker than the bonds of fibrinogen products. Collagen, a connective tissue protein, can be obtained from both living and dead donors. Albumin, a highly nutritive blood component, is easy to collect from a living donor, but hard to separate on an autologous basis. Conversely, platelets and fibrin, which are parts of the normal clotting process, are preferable in this application because they can be collected and separated readily from a simple blood donation.

Preferred methods for making these adhesives depends on the type of adhesive. For example, a platelet adhesive method begins with separating the platelets and plasma from the blood sample, as described in McCullough, Jeffrey, Transfusion Medicine, McGraw-Hill, 1998. The platelets are then processed into a gel form as known in the art for use as an adhesive in the present invention. The American Association of Blood Banks has regulations for making platelet gels and companies such as Medtronics commercially produce them. A preferred method for preparing autologous fibrin adhesives is fibrinogen cryoprecipitation. This process comprises freezing the plasma, followed by thawing to not greater than 4° C. Upon centrifugation, the white precipitate is then ready for use as a fibrin adhesive. An additional method step includes isolation of the autologous thrombin from the blood sample. Bovine thrombin can be used if the recipient has no previous allergic history to bovine proteins.

A beneficial feature of biological adhesives is that the adhesive may be activated simply by the addition of thrombin. Furthermore, the rate of set of the adhesive is determined by the thrombin concentration. The clinical benefit is that these adhesives can be started when desired, manipulated into the desired shape, put in place and set, with all rates easily controlled. Commercially available fibrin adhesive kits are provided with two vials of thrombin, with the 10 IU vial used for slow sets over several minutes, and the 100 or 200 IU vial used for fast sets over several seconds. Synthetic adhesives are activated by other materials to provide the same level of control.

Another beneficial feature of adhesives is that many are absorbed into the body, and this rate of absorption can be controlled by the addition of other agents. For biological adhesives, such agents include the addition of aprotinin in the composition. The clinical benefit is that the adhesives perform their tasks, and then disappear without additional action and without scarring. Another beneficial feature of adhesives is that various surface treatments diminish their adherence to such surfaces. This technique is clinically useful in preventing undesired attachments to instruments, gloves, surrounding tissues, and allows for manipulation of the adhesive compositions containing the embryos. One such surface treatment that can be used with biological adhesives is a concentrated saline solution.

An advantage of platelet adhesives is that platelet adhesives are quite nutritious media, and cause no irritation or inflammation at the point of contact. Platelet adhesives are predictable in terms of bond strength, but their strength is relatively weak. Their strength is determined by the same $\alpha$ and $\beta$ integrin mechanism that determines the adhesive properties of the uterine wall relative to the embryo as described by Tabibzadeh, A., "Patterns of Expression of Integrin Molecules in Human Endometrium Throughout the Menstrual Cycle", Human Reproduction 7(6): 876, 1992.

Platelet adhesive compositions are contemplated by the present invention in part because platelet adhesives are well-suited for direct contact with an embryo due to their high nutritive value and inert bonding. Their relatively low strength of bonding is not much of a hindrance because small, light embryos require little adhesion.

The present invention also comprises compositions comprising fibrin adhesives. Fibrin adhesives have comparatively little nutritive value, and are slightly irritating to tissues. An advantage of fibrin adhesives is their strength, which is greater than that of platelet adhesives. A disadvantage of fibrin adhesives is that the strength of adhesion is unpredictable. An explanation for the unpredictability is that the strength of the adhesive depends upon the square of the fibrinogen concentration. When the fibrinogen is obtained by a cryoprecipitate, the resulting composition has variable amounts of Factor VIII, von Willebrands factor, and other components at lesser concentrations. The present invention contemplates use of fibrin adhesive compositions comprising these factors and other proteins that are found in the cryoprecipitate.

Another embodiment of the present invention includes the use of any biocompatible material in place of the fibrin substrate. The fibrin substrate can be replaced by an artificial substrate consisting of any biocompatible material, such as carbon blocks or fibers. Another option is to include a fibrin adhesive with a fiber matrix. The desired effect is a substrate that is easier to assemble and handle than a fibrin block alone.

The low nutritive value and high strength of fibrin adhesives make them well suited for use as substrates and contact with the uterine wall, which has its own nutrition source. Though it might be thought that irritation due to the fibrin adhesive makes it necessary to avoid contact with the embryo, recent work suggests that some irritation actually improves implantation. See Fioretti, et al, "Fusion Gene Products Encoding Avian Alpha Subunit Inhibin protein, or an Immunogenic Fragment Thereof, and a Carrier Protein", U.S. Pat. No. 5,747,659; 1998. Thus, contact by the fibrin adhesive with the uterine wall is beneficial. Another embodiment of the present invention is to mix the platelet and fibrin adhesives, thereby providing a range of strengths, nutritive values, and site irritations. A preferred method of the present invention comprises having the embryo in close contact with the more nutritious platelet or albumin products, while the fibrin products are used to provide greater strength over longer distances.

The adhesive compositions can be applied to the embryo by using any method that allows for control of the adhesive with little manipulation of the embryo. A preferred method is to directly apply the adhesive composition to embryos that are stabilized in an embryo preparation plate. Another preferred method is to first pour the adhesive composition on a surface and allow the adhesive composition to begin setting up. Second, remove a plug of the adhesive composition that has begun setting and place that plug over the embryo.

Additional adhesive compositions can be added to the embryo as needed to provide support, adhesion or nutrition. For example, after placing a platelet adhesive composition plug over the embryo, a fibrin adhesive composition is poured over the plug/embryo structure so that the fibrin adhesive composition is the outer surface that touches the uterine wall.

A preferred method of encasing embryos for implantation comprises the following steps. An adhesive composition is made and allowed to begin setting. The embryo or embryos are then placed in an embryo preparation plate.

The plate has been prepared so that the adhesives will not stick to the plate. For example, preparation comprises rinsing the plate with a saline solution for easy release of the adhesive. Next, the embryo is placed within a depression in the plate, preferably using micromanipulators, though any known methods of embryo handling equipment are contemplated by the present invention. If the embryo has undergone mechanical assisted hatching, it is placed so that the compromised part of the zona pellucida is facing the bottom of the depression. No particular orientation of the embryo is necessary for the methods of the present invention and any particular required orientation, for example, required in order to facillitate implantation, is contemplated by the present invention.

The adhesive plug is added to the embryo. For example, using an adhesive probe such as the one described in Example II, the cylindrical probe containing the adhesive is then centered over the isolated embryo. The syringe is pressed, thus expelling the adhesive plug. This plug, which is still quite fluid, flows over the embryo and begins to adhere to the embryo wall. The plug is sufficiently set so that it cannot flow into the small space between the embryo and the hemispherical depression. The net result is an embryo with only a selected area covered by a desired amount of adhesive.

In another embodiment, two adhesives may be used. The first adhesive is applied in the manner just described for plug attachment to the embryo. Any of the adhesives, natural or synthetic can be used, though a preferred composition comprises a platelet adhesive. A second adhesive is then applied. Any of the adhesives, natural or synthetic can be used, though a preferred composition comprises a fibrin adhesive. FIGS. 1 and 3 show the resulting embryo encasement using two adhesives.

This method, comprising addition of two adhesives, comprises a first step that uses a probe that deposits an adhesive composition, including but not limited to, a platelet gel layer, on the embryo, and removal of the probe. Next, a larger diameter probe, preferably mounted concentric to the embryo, is used to apply the second adhesive, including but not limited to, a fibrin adhesive. This second probe may also contact a raised ring beyond the boundary of the platelet gel, thus forming a protrusion in the fibrin glue directly over the embryo.

There are many immediate benefits to this two adhesive method, beginning with the improved surface contact provided by two different adhesives. Specifically in this preferred embodiment, the adhesive in direct contact with the embryo is a platelet gel adhesive and the second adhesive is a fibrin adhesive. In addition, the fibrin glue surface beyond the embryo is free to contact the uterine wall.

The unique geometry illustrated in FIG. 3, yields several additional benefits. One such benefit is that the fibrin adhesive layer provides a durable substrate for the weaker platelet gel layer, thus maintaining the desired geometry during transfer of the embryo to the uterine site. In turn, a key feature of this geometry is the protrusion illustrated in the side view of FIG. 3. This protrusion, which is below the elevated fibrin adhesive layer in contact with the uterine wall, forces the embryo and uterine surfaces into very tight contact and improves the chances of implantation. This tension is maintained over time because the durability of the substrate prevents the embryo from recessing excessively into the glue layers.

Another aspect of the present invention is that after the embryo is attached to the adhesive composition or compositions, the embryo at this point is contained within the steel cylinder of the probe. Upon lifting the imbedded probe from the surface, the embryo is usually slightly recessed, thereby protecting the embryo from accidental side contact and subsequent disruption.

Another element of the present invention is an applicator to place the adhesively imbedded embryos within the uterus and attach them to the wall. Features of this device include a means of holding the embryos embedded in adhesive, a means of guiding the device to the desired location and a means of uterine wall attachment.

Of these components, the first is the holding device. The delicate embryo must be protected during transfer, but released when necessary. This can be achieved by including retractable metal retainer pins, as indicated in FIG. 1. These pins, which are sprayed with saline solution for easy release, allow the adhesive layer to be lifted easily from the plate, along with the embedded embryos.

With the pins in place in the applicator, the embryos can then be held at a safe distance from a retractable metal plate, which provides protection from contact with the vaginal or cervical walls during transfer.

During transfer, the assembled applicator and embryo/adhesive load can be guided either by ultrasound or by direct visualization with a hysteroscope. Upon reaching the desired location within the uterus, the embryo and adhesive mixture are then attached with an additional application of an adhesive such as a fibrin adhesive. The adhesive and embryo patch is held closely against the uterine wall by either spring or jack force during this gluing process, thereby preventing additional fibrin glue from seeping into the desired attachment point. The applicator may also incorporate separate activation wires.

Several other embodiments are possible for this method and device. The applicator can incorporate separate guide wires to steer the device to the desired target with minimum trauma to the uterine walls. These guide wires must be oriented to maintain their desired relative positions while they reverse direction upon passing through the vagina, into the cervix, and into the uterine cavity.

The rate of absorption of the adhesive can be slowed by the addition of aprotinin to the adhesive compositions, or increased by the addition of various clot-dissolving enzymes to the adhesive compositions, depending on the conditions required for a given patient.

The adhesive compositions could be intermixed, thereby simplifying the process. For example, in surgical uses, mixed platelet and fibrin adhesives already show some promise for providing both enhanced healing and strength. The adhesives can also incorporate additional nutritive agents and/or antibiotics.

The present invention comprises methods of gluing the embryos to the uterine wall. The net result is that the embryos are in direct contact with a selected point in the uterus for a long period of time. By using biologically compatible materials, rejection is avoided during this process.

It is generally accepted that reduction or elimination of the reduced contact associated with "floating" of the embryo such as are used during prior implantation procedures should be helpful.

Another embodiment of the present invention comprises the use of a transfer device with an applicator. Having prepared the embryo with adhesives, the next step is to transfer this embryo to the patient's uterus. In a preferred embodiment, the transfer device consists of two components: a loader to first gain access to the uterus, and next, an applicator to glue the embryo in place.

The first step of this transfer process is to gain access to the uterus in a safe, sterile and efficient manner. Current practices use a combination of germicidal agents, specula and guide channels. This approach occasionally results in infections and cannot manipulate embryos treated as described herein. A method of the present invention comprises use of germicidal agents and specula, and a unique guide channel through the cervix. In order to comply with anatomical demands and to prevent infections during implantation, the transport loader of FIG. 4 can be used.

As shown in FIG. 4, this device comprises an outer barrel that is flared at one end to prevent over insertion. Inside this barrel is a matching plunger of slightly smaller diameter. A thin film, such as a plastic film, rolled within the plunger, joins the far, or distal ends of the barrel and plunger. The far or distal end of the plunger has three matching leaves, meeting at a dull point.

The first step in using this device is to bend the flexible barrel and plunger into the desired curvature, and then insert the barrel as far as possible into the cervix. The plunger is then pressed, which further penetrates the cervix. Unlike conventional probes, however, the enclosed film unrolls during this process. Because this film, instead of the plunger itself, contacts the cervix, there is no entrainment of contaminants. This continuous dispensing of the film also prevents the delicate cervical tissues from being drawn along with the plunger, thereby increasing patient comfort. The pointed end of the plunger also improves patient comfort by gradual opening of the channel. Upon full insertion into the uterus these leaves flare outward, providing a secure anchor effect and a tapered entry and exit path, which aids in the insertion and removal of the applicator described below.

Additional embodiments of this device include germicidal and/or anesthetic agents on the film, thus resulting in smooth, uniform application. With such modifications, this device could thus be used in a wide variety of gynecological procedures, as well as various urologic and respiratory applications.

Having gained access to the uterus through the hollow plunger, the next step is to attach the embryos in place on the uterine wall. This is the task of the second component of the transfer instrument, the applicator.

Like the above loader, this component requires anatomical considerations. A preferred instrument comprises a small, flexible device, capable of negotiating the narrow cervical canal while adapting to the angle between the vagina and uterus. The simplest such device is a thin plastic tube, like those currently used in IVF practice. In current practice, however, the suspended embryos are simply squirted into the uterus through this tube, but this technique will not work with embryos in adhesives. Furthermore, the current technique provides no control of the implantation site, whereas the present invention allows for embryo attachment at a selected location.

One alternative is to attach the embryo to the end of the plastic tube, and then insert the tube all the way through the uterine cavity to the opposing wall. The adhesive would then bond to the wall, and the instrument would be withdrawn. There are essential considerations that must be taken into account when using this method, such as determining the proper insertion depth. If the probe is only millimeters or even less away from the wall, the glued embryo will not attach properly, leading to implantation failure. Conversely, if the probe is inserted too deeply, the embryo could be forced into the glue or possibly even crushed. Even worse, slightly deeper insertion could result in uterine perforation, a very dangerous complication. With proper control, such as use of viewing instruments and/or tactile control, this method of implantation can be utilized.

The central mid-section of the uterus is the desired implantation site, and an applicator that can provide embryos for attachment at this site is preferred. To reach these walls, the implantation unit must therefore be capable of gluing the embryo at right angles, but action at right angles is mechanically difficult.

In an embodiment of the device of the present invention, mounting the glue application barrel at right angles to the insertion probe resolves the action angle problem. The barrel can be bent or miter cut to form a 90° angle. Although the hydraulic drive on the plunger works through any angle, there is still the potential problem that the barrel may not be aligned normal to the wall plane, thereby not properly placing the embryo. There is also the potential problem that the curvature of the flexible probe may leave the barrel too far away from the uterine surface for effective placement.

The application instrument can be modified to allow embryo placement at the top as well as the bottom of the inserted unit. The advantage of this approach is that the embryos can be placed on opposite sides of the uterus, which is the ideal placenta location for twins in case both embryos implant.

Figure 5:
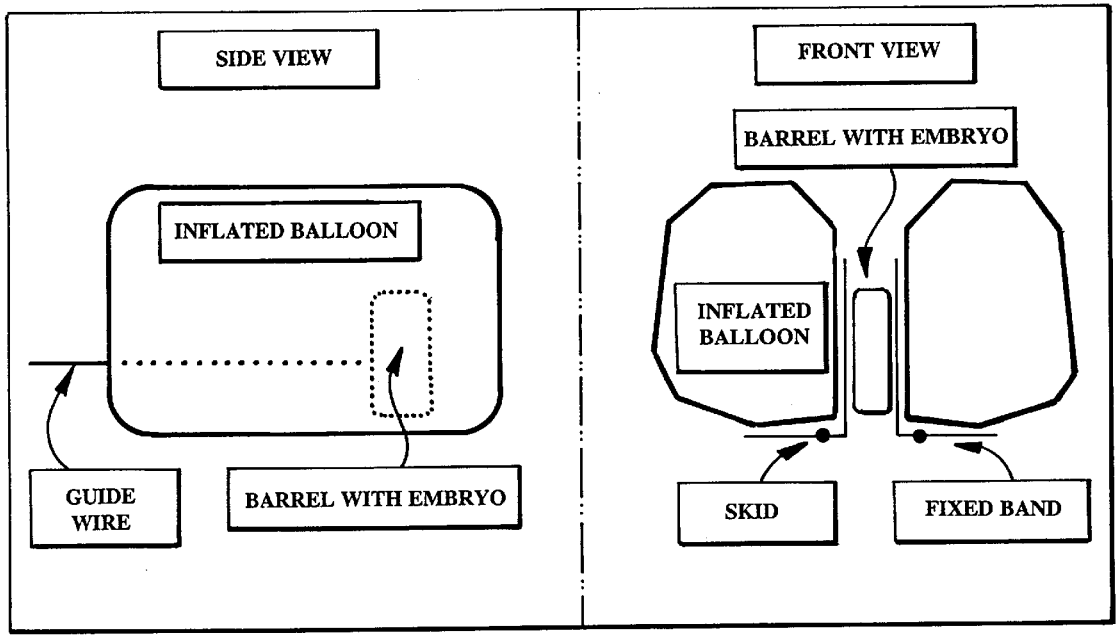
FIG. 5 shows an embodiment of an embryo transfer applicator.

A device of the present invention mounts a pair of balloons on opposite sides of the insertion probe, as illustrated in FIG. 5. Using the technology employed for balloon angioplasty, the opposed balloon pair thereby fills the intrauterine space. The inflatable balloon may include reinforcing ribs so that all of the balloon material can be safely removed even if the balloon ruptures. This fixed alignment of the balloons aligns the probe directly at the wall. To ensure proper wall contact, fixed bands on the side of the balloons, near the barrel exit, force the expansion in the opposite direction. Complete expansion forces the barrel directly, but gently, against the uterine wall. Upon complete expansion, plastic strips glued to the bottom of the balloons on opposite sides of the barrel maintain the barrel at the proper location throughout the attachment process. In addition, these strips act as skids, allowing the unit to be repositioned by pulling or pushing the guide wire even with the balloons inflated.

There is a sheath around the entire guide wire, to form a conduit from outside the body all the way to the applicator tip. This conduit provides a means of loading prepared barrels after the applicator is in place, thereby avoiding potential loss of the embryo during the insertion and placement of the applicator. In addition, this device also provides a means to attach more than one embryo without removing and replacing the entire applicator.

In summary, the methods of the present invention comprise a first step of preparing the embryos with adhesives, and then containing each embryo in a separate barrel, tube and syringe assembly. Simultaneous to this laboratory work, the patient is to be prepared in the clinic. As described, the first clinical step is to insert the loader into the patient. Next the transfer applicator is inserted and guided into place under ultrasound imaging. Fiber optic viewing can also be used for correct placement. Once the applicator is in place, the balloons are inflated.

Using the current patient/embryo identification matching procedures, the first prepared embryo is handed from the laboratory technician to the attending physician. The physician passes the mounted embryo through the conduit along the guide wire until the barrel assembly reaches the far tip of the instrument. The saline syringe will then be activated, thus displacing the plunger and forcing the glued embryo into contact with the uterine wall. This configuration is maintained while the glue bonds to the wall, for approximately 2–20 minutes, preferably about 2–10 minutes and most preferably, about 3 to 5 minutes. The saline syringe is then pulled back to retract the plunger and release the embryo. The guide wire is withdrawn about 1 cm, drawing the balloon assembly along on its skids. The entire applicator passes over the attached embryo without risk of dislodging it.

This attachment method is then repeated for the next embryo or embryos. After the last embryo is in place, the balloons are deflated, and the applicator is removed through the loader. The loader is then removed from the cervix, completing the transfer procedure.

It is contemplated by the present invention that embryos prepared with the adhesive compositions of the present invention can be implanted into the patient by any means known to those skilled in the art and the present invention is not limited by the devices or methods for implantation taught herein. Additionally, the present invention contemplates that the methods and devices for implanting embryos that are taught herein can be used for other procedures involving humans or animals wherein a controlled manipulation within an internal space is needed. For example, such controlled manipulations may be needed in urinary, gastric or other gynecological procedures.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

A Method of Adhesive Attachment

An embodiment of a preferred method is described here and the device used was as shown in FIG. 1. A test cell mass, that resembles an embryo in size and cellular fragility, was used in place of an actual embryo. With the test cell mass in position in the hemispheric depressions of the embryo preparation plate, a thin layer of platelet or albumin adhesive was applied. Because of the viscoelastic behavior of these materials, only the top half of the test cell mass was coated. This arrangement complemented the half-submerged geometry of normally implanted embryos. This coating procedure would leave any AH sectors uncovered, given the orientation described above.

Next, a thin layer of fibrin glue was applied, consisting of a mixture of fibrinogen and thrombin. This mixture was dispensed by conventional dual cylinder applicators. For rapid clot formation, approximately 200 units of thrombin were used for each cc of applied fibrinogen.

A metallic sleeve was then placed around the half-coated embryo, penetrating down to the base of the incubation plate. For easy release from the fibrin bonds, this sleeve was sprayed with saline solution.

The sleeve was either small and circular in cross section to remove a single test cell mass, or large and extended to remove an entire set of test cell masses. In either case, the net result was that the test cell masses were half-submerged in an adhesive layer. This layer was readily lifted from the incubation plate, with the test cell masses exposed on one common side, which was again oriented downward for AH.

Example 2

A Method of Encasing an Embryo in Adhesives

The method was to form a thin layer of adhesive and then this layer was attached to one side of the test cell mass. To accomplish this, first, the adhesive components were mixed. Next, a thin layer of glue was spread on a flat Teflon surface, which was previously rinsed with saline solution for easy glue release. The glue was then allowed to begin to harden, as evidenced by the formation of striations of varying thickness across the surface.

A probe was used to extract a specified amount of the glue in a specified shape. This probe was constructed of a 2 mm length of stainless steel cut tube from a hypodermic syringe. The remaining part of the syringe was then forced through a 1.5 mm thick layer of rubber, thus forming a sealed plunger. This plunger was then inserted into the probe, where it was retained by a crimp at each end. The far end of the probe was attached to a 15 cm length of flexible plastic tubing, the opposite end of which was connected to a syringe filled with saline solution. Pressing and pulling the syringe plunger thus caused the rubber plunger inside the probe to move the entire length of the barrel in the corresponding direction. The system was then cycled repeatedly at high syringe pressure so that the rubber plunger was eroded sufficiently to protrude 0.75 mm beyond the tube at maximum extension.

When no further striations develop in the adhesive, the assembled probe was inserted through the thickest part of a striation, progressing slightly beneath the plastic surface. The remaining adhesive, which had not yet reached the point of tack, was then rinsed from the plate. Without the surrounding adhesive, the probe can then be lifted cleanly from the plate surface. When operated with pre-mounted jigs, this procedure took a few seconds to complete.

The net result was a small, well-defined plug of adhesive. This plug was allowed to remain in the probe barrel for a few minutes and approach tack. The next step was to apply the resulting cylindrical plug layer of glue onto the test cell mass. Use of this type of adhesive plug is shown in FIG. 2.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of embryo implantation comprising:
   (a). placing an adhesive composition on an embryo prior to implantation; and
   (b). implanting the embryo in the uterus of an animal.

2. The method of claim 1 wherein the adhesive composition comprises one type of adhesive.

3. The method of claim 2, wherein the one type of adhesive is fibrin.

4. The method of claim 2, wherein the one type of adhesive is albumin.

5. The method of claim 2, wherein the one type of adhesive is platelet adhesive.

6. The method of claim 1, wherein the adhesive composition comprises two types of adhesives.

7. The method of claim 6, wherein the adhesive composition comprises fibrin and platelet adhesives.

8. The method of claim 6, wherein the adhesive composition comprises fibrin and albumin adhesives.

9. The method of claim 1, wherein the adhesive composition comprises the admixture of two adhesives.

10. The method of claim 1, wherein the adhesive composition further comprises compositions to retard or enhance absorption of the adhesive composition.

11. A method of implantation of embryos comprising,
    a) applying an adhesive composition to an embryo to form an adhesive/embryo structure;
    b) administering the adhesive/embryo structure to the uterus of a mammal; and
    c) allowing the adhesive/embryo structure to bond to the uterus wall.

12. The method of claim 11 wherein the adhesive composition comprises one type of adhesive.

13. The method of claim 12, wherein the one type of adhesive is selected from a group consisting of fibrin and albumin.

14. The method of claim 12, wherein the one type of adhesive is platelet adhesive.

15. The method of claim 11, wherein the adhesive composition comprises two types of adhesives.

16. The method of claim 15, wherein the adhesive composition comprises fibrin and platelet adhesives.

17. The method of claim 15, wherein the adhesive composition comprises fibrin and albumin adhesives.

18. The method of claim 11, wherein the adhesive composition comprises admixture of two adhesives.

19. The method of claim 11, wherein the adhesive composition further comprises compositions to retard or enhance absorption of the adhesive composition.

20. A device for implanting at least one embryo in the uterus of an animal comprising:
    a) means to gain access to the uterus;
    b) means for holding at least one embryo;
    c) means to guide the device to the desired location; and
    d) means to contact the embryo with the surface of the uterus;
    wherein the device is capable of holding the embryo in continuous contact with a selected point of the uterus, and;
    wherein the means for holding the embryo comprises adhesive.

21. The device for implanting an embryo of claim 20 wherein the means to gain access is flexible.

22. The device of claim 20 further comprising at least one inflatable balloon mounted on the means to gain access.

23. The device of claim 22 comprising two or more inflatable balloons mounted on opposing sides of the means to gain access.

24. The device of claim 22 wherein the inflatable balloon further comprises reinforcing ribs.

25. The device of claim 20 wherein the means for holding the embryo further comprises a retractable means for attachment of the embryo holding means to the implanting device.

26. A device for implanting at least one embryo in the uterus of an animal comprising:

a) means to gain access to the uterus;

b) means for holding at least one embryo;

c) means to guide the device to the desired location; and d) means to contact the embryo with the surface of the uterus;

wherein the device is capable of holding the embryo in continuous contact with a selected point of the uterus, and;

wherein the guide means comprises at least two separate structures capable of maintaining a position relative to the contact means while reversing direction.

27. The device ol claim 26 further comprising a roll of a film wherein the distal end of the guide means is attached to one end of the film and the distal end of the means to contact the embryo is attached to the opposite end of the film.

* * * * *